(12) United States Patent
Perrier et al.

(10) Patent No.: US 6,548,170 B2
(45) Date of Patent: Apr. 15, 2003

(54) TREATED WATER-INSOLUBLE SOLID PARTICLES, PREPARATION AND USE

(75) Inventors: Eric Perrier, Les Cotes d'Arey (FR); Lysiane Tholon, Miribel (FR); Nabil Abdul Malak, Caluire (FR)

(73) Assignee: Coletica, Lyons (FR)

( * ) Notice: Subject to any disclaimer, the term of this patent is extended or adjusted under 35 U.S.C. 154(b) by 0 days.

(21) Appl. No.: 09/909,438

(22) Filed: Jul. 19, 2001

(65) Prior Publication Data
US 2003/0049447 A1 Mar. 13, 2003

(30) Foreign Application Priority Data
Jun. 5, 2001 (FR) ............................................. 01 07336

(51) Int. Cl.$^7$ ................................................. B32B 5/16
(52) U.S. Cl. ................. 428/402; 428/402.24; 428/403; 428/407; 424/401; 424/418; 424/485; 424/490; 424/491; 424/492; 424/493; 424/494; 424/495; 424/499; 264/4.1; 264/4.3; 264/4.32; 264/4.7
(58) Field of Search .............................. 428/402.24, 402, 428/403, 407; 424/401, 418, 485, 490, 491, 492, 493, 494, 495, 499; 264/4.1, 4.3, 4.32, 4.7

(56) References Cited

U.S. PATENT DOCUMENTS

| 4,599,114 A | 7/1986 | Atkinson | 106/448 |
|---|---|---|---|
| 4,640,943 A | 2/1987 | Meguro et al. | 523/200 |
| 4,711,783 A | 12/1987 | Huc et al. | 424/460 |
| 4,909,582 A | 3/1990 | Atkinson | 385/146 |
| 5,912,016 A | * 6/1999 | Perrier et al. | 424/489 |
| 6,132,750 A | * 10/2000 | Perrier et al. | 424/418 |
| 6,197,757 B1 | * 3/2001 | Perrier et al. | 514/53 |

FOREIGN PATENT DOCUMENTS

| EP | 0 139 481 | 5/1985 |
|---|---|---|
| FR | 2 522 986 | 9/1983 |
| GB | 930 421 | 7/1963 |
| GB | 1 012 513 | 12/1965 |
| GB | 1 393 721 | 5/1975 |
| WO | WO 01/30888 | 10/2000 |

OTHER PUBLICATIONS

Patent Abstracts of Japan & JP 62 262740. Microcapsule or Matrix Granulated Powder Having Wall Film Composed of Shellac, Nov. 14, 1987.

* cited by examiner

*Primary Examiner*—Leszek Kiliman
(74) *Attorney, Agent, or Firm*—Merchant & Gould P.C.

(57) ABSTRACT

The present invention relates to water-insoluble solid particles, especially pigments, which characteristically are coated with at least one layer of at least one product resulting from the reaction between at least one molecule capable of becoming hydrated in contact with water and at least one lipophilic molecule. It further relates to cosmetic, pharmaceutical and agricultural compositions comprising such particles and to the manufacture and use of said particles.

50 Claims, No Drawings

TREATED WATER-INSOLUBLE SOLID PARTICLES, PREPARATION AND USE

The present invention relates essentially to water-insoluble solid particles coated with at least one layer of at least one product resulting from the reaction between a molecule capable of becoming hydrated in contact with water and at least one lipophilic molecule, and to their use for the manufacture of cosmetic compositions, pharmaceutical compositions or agricultural compositions. These water-insoluble solid particles are preferably used to manufacture anhydrous cosmetic compositions, making it possible to incorporate hydrating molecules into formulations which are generally dehydrating.

PRIOR ART

The surface treatment of pigments is a technique widely used in the industrial sector. This surface treatment can make it possible for example to improve drying and coverage in the paints sector. Surface treatments of pigments are also technologies used in the cosmetics sector, for example for improving the ability of pigments to be incorporated into cosmetic formulations, or for increasing the adhesion of the pigments to the skin.

Thus, for example, pigments coated with different types of silicones are proposed commercially as cosmetic pigments for make-up applications, the aim being to facilitate the incorporation of the pigments into generally hydrophobic formulations for which the untreated (conventional) pigments generally have little affinity. Thus titanium dioxides coated with silicone polymers and zinc oxides coated with silicone polymers are currently very widely used in cosmetics, particularly in sun protection preparations, which generally contain large amounts of these pigments (it generally being complicated to incorporate said pigments into cosmetic formulations at very high concentrations).

Likewise, some pigments coated with fluorocarbon polymers are also proposed commercially as cosmetic pigments for make-up applications, the aim being to improve their adhesive power while at the same time enabling the formulations to form a film on application (for example the film left by a lipstick or make-up foundation).

It is also possible to find pigments coated with natural polymers such as proteins in general and collagen in particular. The coating of insoluble particles with collagen films has been described in particular in patent U.S. Pat. No. 4,711,783 to Huc et al. These coatings are generally rather unfavorable for the adhesion of the pigments to the skin, and they give rise to manufacturing problems when they are incorporated into make-up formulations. In fact, their hydrophilic nature renders the pigments more hydrophilic on the surface, making the treated pigments more difficult to disperse in the hydrophobic phases which are present in most if not all formulations of make-up preparations.

However, this type of coating is valuable because it enables molecules or macromolecules such as proteins to be introduced into formulations which are generally anhydrous or have a low water content, said molecules or macromolecules themselves being capable of trapping very substantial amounts of water and hence of moisturizing the skin very considerably after application of the products containing them.

This ability to introduce molecules of very high moisturizing power into formulations, particularly anhydrous formulations, is becoming crucial. In fact, the use of volatile molecules, particularly volatile silicones, at a very high concentration in anhydrous formulations, which make it possible to avoid transfer of the pigments onto white surfaces (property of "no transfer"), also gives rise to very dry formulations which are rather uncomfortable and rather unpleasant when applied. Any substance which makes it possible to counteract these unpleasant sensations on application and to improve the cosmetic feel, particularly in so-called "no transfer" formulations, is of very great interest to those skilled in the art.

OBJECTS OF THE INVENTION

One main object of the invention is to solve the new technical problem consisting in the provision of a novel formulation of water-insoluble solid particles having a good dispersibility in hydrophilic media, hydrophilic molecules or molecules with a very high moisturizing power, enabling the formulation to be used in the cosmetic or pharmaceutical sector or in agriculture.

Another main object of the present invention is to solve the new technical problem consisting in the provision of novel formulations of water-insoluble solid particles combined with hydrophilic molecules, while at the same time preserving an adhesion capacity and avoiding the problem of transfer, especially where pigments are involved.

Another main object of the present invention is to solve the new technical problem consisting in the provision of novel solid particles such as pigments, improving the compatibility with mostly hydrophobic phases.

The invention makes it possible for the first time to solve all these technical problems in a simple and relatively inexpensive manner which can be used on the industrial scale, especially in cosmetics or pharmaceutics or in agriculture.

Thus the invention proposes to solve the above technical problems, namely to introduce hydrophilic molecules, or even hydrophilic polymers, into the lipophilic phases of emulsions or into anhydrous formulations, while at the same time preserving a good dispersibility of the pigments, with the aim of providing softness and homogeneous spreading on application.

In fact, to improve the contact between the hydrophilic polymers used to coat the pigments, on the one hand, and the formulation consisting of mostly hydrophobic phases (silicones or synthetic or vegetable oils), on the other hand, the inventors attempted to graft fatty chains onto these natural polymers. The lipophilic polymers were formed either before being used to coat the pigments, or directly in the presence of the pigment to be treated, so as to enhance the interactions between the three compounds. The galenical properties of formulations containing one or other of these two complexes formed in this way were compared with the galenical properties of formulations containing each of the compounds separately, and unexpected properties were obtained in these studies, which are presented below.

According to a first feature, the present invention provides water-insoluble solid particles which are coated with at least one product resulting from the reaction between at least one of said molecules capable of becoming hydrated in contact with water and at least one lipophilic molecule.

In one advantageous embodiment, the lipophilic molecule is a hydrocarbon organic molecule having from 4 to 30 carbon atoms which is reacted in a reactive form with the molecule capable of becoming hydrated in contact with water.

In another advantageous embodiment, the water-insoluble solid molecules are selected from an organic or mineral pigment, a mineral filler such as talcum, a physical sun filter such as a metal oxide, particularly a zinc oxide or a titanium dioxide, and a chemical sun filter.

In yet another advantageous embodiment, the molecule capable of becoming hydrated in contact with water is selected from an amino acid, a peptide, particularly with a molecular weight of less than 5000 Daltons, a protein, a polysaccharide, an oligosaccharide, a gum, a vinylic polymer and a fluorinated polymer.

In yet another advantageous embodiment, the above-mentioned protein has an average molecular weight equal to or greater than 5000 Daltons and less than 1,000,000 Daltons, preferably less than 300,000 Daltons, and is selected in particular from collagen, gelatin, albumin, ovalbumin, elastin, reticulin, fibronectin, keratin, silk, laminin, desmosin and isodesmosin, proteoglycans of the extracellular matrix, glycosaminoglycans such as hyaluronic acid, caseins, lactalbumin, lactoglobulins, enzymes extracted from animal tissues, a protein derived from plants, such as wheat protein, unicellular or multicellular alga protein, maize protein, pea protein, lupin protein, bean protein, horse bean protein, cotton protein, almond protein, soya protein, sunflower protein, alfalfa protein and oat protein; cellulose and derivatives thereof such as alkyl or hydroxyalkyl cellulose, notably ethyl cellulose, hydroxyethyl cellulose, propylcellulose, and hydroxypropylcellulose; chitosan and derivatives thereof such as alkyl or hydroxyalkyl chitosan, notably hydroxypropyl chitosan, starch, maltodextrin, polyvinyl alcohol and a polyvinylpyrrolidone, and mixtures thereof.

In yet another advantageous embodiment, the above-mentioned lipophilic molecule is an organic molecule having from 4 to 30 carbon atoms, particularly a hydrophobic, saturated or unsaturated, linear, branched or cyclic $C_4$–$C_{30}$ lipophilic fatty molecule which can be converted to a reactive form such as a $C_4$–$C_{30}$ fatty alkyl halide, $C_4$–$C_{30}$ fatty acid halide or $C_4$–$C_{30}$ fatty acid anhydride.

In yet another advantageous embodiment, the above-mentioned lipophilic molecule is selected from a $C_4$–$C_{30}$ fatty acid, particularly butyric acid, pentanoic acid, hexanoic acid, heptanoic acid, octanoic acid, nonanoic acid, decanoic acid, dodecanoic acid, lauric acid, myristic acid, palmitic acid, stearic acid, ricinoleic acid, oleic acid, linoleic acid, linolenic acid or undecylenic acid, and the corresponding $C_4$–$C_{30}$ fatty alcohols and fatty amines, derivatives, notably esters, of said fatty acids, of said fatty alcohols and of said fatty amines, and mixtures thereof, preferably lauric, stearic or palmitic acid and especially a mixture of stearic and palmitic acids, laurylamine or hexadecylamine, or decyl alcohol.

In yet another advantageous embodiment, the molecules capable of becoming hydrated in contact with water are first introduced into an aqueous medium, in which they are dissolved or dispersed, after which they are reacted with said lipophilic molecules in reactive form until said reaction product is formed, and then said water-insoluble solid particles are added to the medium containing the reaction product and are dispersed by any means of dispersion, especially by mechanical dispersion.

In yet another advantageous embodiment, the molecules capable of becoming hydrated in contact with water are introduced into an aqueous medium until they have dissolved or dispersed, then said water-insoluble solid particles are dispersed in said aqueous medium, and finally said lipophilic molecules in reactive form are introduced into the aqueous medium to give said reaction product, said water-insoluble solid particles thereby being coated with said reaction product.

In yet another advantageous embodiment, the aqueous medium containing said water-insoluble solid particles coated with said reaction product is adjusted to a pH compatible with a given industrial use, particularly a cosmetic use or a pharmaceutical use or else an agricultural use.

In yet another advantageous embodiment, the aqueous medium containing said water-insoluble solid particles coated with said reaction product is dried by any drying means, particularly by atomization, lyophilization or dehydration under vacuum and preferably by lyophilization.

In yet another advantageous embodiment, the dried product is ground until the particle size is less than or equal to about 200 $\mu$m.

In yet another advantageous embodiment, the pigment is coated with at least one layer of at least one product resulting from the reaction between at least one molecule capable of becoming hydrated in contact with water and at least one lipophilic molecule.

In yet another advantageous embodiment, said solid particles comprise a white or colored organic pigment, or a white or colored mineral pigment such as titanium dioxide, zinc oxide, chromium oxide or black, yellow or blue iron oxide, or a mineral filler used particularly for make-up, such as talcum, kaolin, mica, boron nitride, nylon beads, silica, silica beads, said pigment or filler being coated with at least one layer of the product resulting from the reaction of a gum lac with a halide of butyric, capric, caprylic, decanoic, lauric, stearic, myristic, palmitic, oleic, linoleic, linolenic, undecylenic or undecanoic acid.

In yet another advantageous embodiment, said solid particles comprise a white or colored organic pigment, or a white or colored mineral pigment such as titanium dioxide, zinc oxide, chromium oxide or black, yellow or blue iron oxide, or a mineral filler used particularly for make-up, such as talcum, kaolin, mica, boron nitride, nylon beads, silica, silica beads, said pigment or filler being coated with at least one layer of the product resulting from the reaction of hyaluronic acid with a halide of butyric, capric, caprylic, decanoic, lauric, stearic, myristic, palmitic, oleic, linoleic, linolenic, undecylenic or undecanoic acid.

In yet another advantageous embodiment, said solid particles comprise a white or colored organic pigment, or a white or colored mineral pigment such as titanium dioxide, zinc oxide, chromium oxide or black, yellow or blue iron oxide, or a mineral filler used particularly for make-up, such as talcum, kaolin, mica, boron nitride, nylon beads, silica or silica beads, said pigment or filler being coated with at least one layer of the product resulting from the reaction of an acacia gum with a halide of butyric, capric, caprylic, decanoic, lauric, stearic, myristic, palmitic, oleic, linoleic, linolenic, undecylenic or undecanoic acid.

In yet another advantageous embodiment, said solid particles comprise a white or colored organic pigment, or a white or colored mineral pigment such as titanium dioxide, zinc oxide, chromium oxide or black, yellow or blue iron oxide, or a mineral filler used particularly for make-up, such as talcum, kaolin, mica, boron nitride, nylon beads, silica or silica beads, said pigment or filler being coated with at least one layer of the product resulting from the reaction of polyvinyl alcohol with a halide of butyric, capric, caprylic, decanoic, lauric, stearic, myristic, palmitic, oleic, linoleic, linolenic, undecylenic or undecanoic acid.

In yet another advantageous embodiment, said solid particles comprise a white or colored organic pigment, or a white or colored mineral pigment such as titanium dioxide, zinc oxide, chromium oxide or black, yellow or blue iron oxide, or a mineral filler used particularly for make-up, such as talcum, kaolin, mica, boron nitride, nylon beads, silica or silica beads, said pigment or filler being coated with at least one layer of the product resulting from the reaction of a polyvinylpyrrolidone with a halide of butyric, capric, caprylic, decanoic, lauric, stearic, myristic, palmitic, oleic, linoleic, linolenic, undecylenic or undecanoic acid.

In yet another advantageous embodiment, said solid particles comprise a white or colored organic pigment, or a white or colored mineral pigment such as titanium dioxide, zinc oxide, chromium oxide or black, yellow or blue iron oxide, or a mineral filler used particularly for make-up, such as talcum, kaolin, mica, boron nitride, nylon beads, silica or silica beads, said pigment or filler being coated with at least one layer of the product resulting from the reaction of an agar with a halide of butyric, capric, caprylic, decanoic, lauric, stearic, myristic, palmitic, oleic, linoleic, linolenic, undecylenic or undecanoic acid.

In yet another advantageous embodiment, said solid particles comprise a white or colored organic pigment, or a white or colored mineral pigment such as titanium dioxide, zinc oxide, chromium oxide or black, yellow or blue iron oxide; or a mineral filler used particularly for make-up, such as talcum, kaolin, mica, boron nitride, nylon beads, silica or silica beads, said pigment or filler being coated with at least one layer of the product resulting from the reaction of a gel of aloe vera with a halide of butyric, capric, caprylic, decanoic, lauric, stearic, myristic, palmitic, oleic, linoleic, linolenic, undecylenic or undecanoic acid.

In yet another advantageous embodiment, said solid particles comprise a white or colored organic pigment, or a white or colored mineral pigment such as titanium dioxide, zinc oxide, chromium oxide or black, yellow or blue iron oxide, or a mineral filler used particularly for make-up, such as talcum, kaolin, mica, boron nitride, nylon beads, silica or silica beads, said pigment or filler being coated with at least one layer of the product resulting from the reaction of a starch or maltodextrin with a halide of butyric, capric, caprylic, decanoic, lauric, stearic, myristic, palmitic, oleic, linoleic, linolenic, undecylenic or undecanoic acid.

According to a second feature, the present invention provides the use of the water-insoluble solid particles coated with at least one layer of said product resulting from the reaction between a molecule capable of becoming hydrated in contact with water and a lipophilic molecule, for the manufacture of a cosmetic composition, a pharmaceutical composition, a food composition or an agricultural composition, preferably for the manufacture of a cosmetic composition.

In one advantageous embodiment, the water-insoluble solid particles are used for the manufacture of a cosmetic composition, particularly an anhydrous cosmetic composition such as a lipstick or make-up foundation.

In one advantageous embodiment, the water-insoluble solid particles coated with the above-mentioned reaction product are first dispersed in a mineral oil such as vaseline, an organic oil, particularly a fatty acid ester such as nonanoyl isononanoate or caprylic/capric triglyceride, a vegetable oil, particularly castor oil, or a silicone, particularly a volatile silicone.

According to a third feature, the present invention also covers a cosmetic composition which comprises water-insoluble solid particles coated with at least one layer of at least one product resulting from the reaction between a molecule capable of becoming hydrated in contact with water and at least one lipophilic molecule as defined above or as described below.

According to a fourth feature, the present invention also covers a pharmaceutical composition which comprises water-insoluble solid particles coated with at least one layer of at least one product resulting from the reaction between a molecule capable of becoming hydrated in contact with water and at least one lipophilic molecule as defined above or as described below.

According to a fifth feature, the present invention also covers an agricultural composition which comprises water-insoluble solid particles coated with at least one layer of at least one product resulting from the reaction between a molecule capable of becoming hydrated in contact with water and at least one lipophilic molecule as defined above or as described below.

According to a sixth feature, the present invention also covers a process for the manufacture of the water-insoluble solid particles coated with at least one layer of at least one product resulting from the reaction between at least one molecule capable of becoming hydrated in contact with water and at least one lipophilic molecule as defined above or as described below, said process comprising a step in which said water-insoluble solid particles are coated with a product resulting from the reaction between said molecule capable of becoming hydrated in contact with water and said lipophilic molecule. Within the framework of the process, the reaction product can be formed after the solid particles have been mixed with the molecule capable of becoming hydrated in contact with water in an aqueous medium, or said reaction product has been formed prior to admixing said solid particles.

The reaction conditions are well known to those skilled in the art and are e.g. those described in prior art document FR-A-2 739 860 to the Applicant, or they are clearly apparent to those skilled in the art from the Examples of manufacture below.

Other objects, characteristics and advantages of the invention will be clearly apparent from the following explanatory description referring to the currently preferred embodiments of the invention, which are given simply by way of illustration and cannot therefore in any way limit the scope of the invention. In the Examples, unless indicated otherwise, the percentages are given by weight, the temperature is in degrees Celsius or is room temperature, and the pressure is atmospheric pressure.

EXAMPLE 1

Products of the Invention from Gum Lac 1a) 10 g of commercial dewaxed gum lac (Sigma) are poured slowly into demineralized water (100 ml to 1 liter) at a controlled temperature of between 15° C. and 90° C. and at atmospheric pressure, with slow mechanical agitation (10–1000 rpm). When it has completely dissolved (from 5 minutes at 90° C. to 3 hours at 15° C.), the pH of the solution is adjusted to a value of between 7 and 12 (preferably to a value of between 10 and 11) with a base such as a strong base, for example KOH or NaOH.

1b) After stabilization of the pH, 40 g of commercial stearoyl chloride (Sigma) are added slowly at a controlled temperature of between 15 and 90° C. and at atmospheric pressure, with agitation.

1c) During the reaction, the pH is adjusted to a value of between 7 and 12, preferably of between 10 and 11.

1d) 50 g of a commercially available organic pigment (DC Red 7, LCW France) are then added to the mixture at a controlled temperature of between 15° C. and 90° C. and at atmospheric pressure, with slow mechanical agitation (10–1000 rpm).

1e) The pH is then adjusted to a value of between 5 and 7 with HCl or NaOH.

1f) The product is lyophilized and the powder obtained (about 110 g) is ground to a particle size equal to or less than 200 microns. The ground powder is used either as such, or sterilized by beta or gamma radiation, or dispersed in a mineral oil (vaseline), an organic oil (a fatty acid ester such as nonanoyl isononanoate or caprylic/capric triglycerides), a vegetable oil (castor oil) or a silicone (volatile silicone).

EXAMPLE 2

Other Products of the Invention from Gum Lac

2a) As described in 1a) above.

2b) 50 g of a commercially available organic pigment (DC Red 7, LCW France) are then added to the mixture at a controlled temperature of between 15° C. and 90° C. and at atmospheric pressure, with slow mechanical agitation (10–1000 rpm).

2c) After stabilization of the pH to a value of between 7 and 12, preferably of between 10 and 11, 40 g of commercial stearoyl chloride (Sigma) are added slowly at a controlled temperature of between 15 and 90° C. and at atmospheric pressure, with agitation.

2d) During the reaction, the pH is adjusted to a value of between 7 and 12, preferably of between 10 and 11.

2e) The pH is then adjusted to a value of between 5 and 7 with HCl or NaOH.

2f) The product is lyophilized and the powder obtained (about 110 g) is ground to a particle size equal to or less than 200 microns. The ground powder is used either as such, or sterilized by beta or gamma radiation, or dispersed in a mineral oil (vaseline), an organic oil (a fatty acid ester such as nonanoyl isononanoate or caprylic/capric triglycerides), a vegetable oil (castor oil) or a silicone (volatile silicone).

EXAMPLE 3

Other Products of the Invention from Gum Lac

The product of the invention is prepared as described in Examples 1 and 2 except that the proportions of gum lac/stearoyl chloride/pigment are different: the respective weights of the 3 constituents used in the two Examples above are 10/40/50 (w/w/w, in g/100 g of product of the invention). In this Example the weight of gum lac varies between 0.1 and 70 g/100 g, the weight of stearoyl chloride varies from 0.1 to 90 g/100 g and the weight of pigment varies from 10 to 99 g/100 g.

EXAMPLE 4

Other Products of the Invention from Gum Lac

The product of the invention is prepared as described in Examples 1, 2 and 3 except that the nature of the acid is different: the chloride of butyric, capric, caprylic, decanoic, lauric, myristic, palmitic, oleic, linoleic, linolenic, undecylenic or undecanoic acid, or of any other saturated or unsaturated, linear, cyclic or branched fatty acid, is used.

Likewise, all other things being identical, the anhydrides of the acids described above are successfully used in Examples 1, 2 and 3 above.

EXAMPLE 5

Other Products of the Invention from Gum Lac

The product of the invention is prepared as described in Examples 1, 2, 3 and 4 except that the nature of the pigment is different: a commercial organic pigment other than DC Red 7, or a commercial mineral pigment (titanium dioxide, zinc oxide, chromium oxide, black, yellow or blue iron oxides, etc.), or compounds described in make-up products as fillers (talcum, kaolin, mica, boron nitride, nylon beads, silica, silica beads, etc.), are used.

EXAMPLE 5a

The product is prepared by following the protocol of Example 2; the ingredients used are gum lac (10 g/100 g), stearoyl and palmitoyl chloride used as a 60/40 (w/w) mixture (40 g/100 g) and titanium dioxide (50 g/100 g).

EXAMPLE 5b

The product is prepared by following the protocol of Example 2; the ingredients used are gum lac (30 g/100 g), stearoyl and palmitoyl chloride used as a 60/40 (w/w) mixture (20 g/100 g) and titanium dioxide (50 g/100 g).

EXAMPLE 6

Other Products of the Invention from Hyaluronic Acid

The product of the invention is prepared as described in Examples 1 to 5 except that the nature of the hydrophilic polymer is different: hyaluronic acid is used.

The preferred product is prepared by following the protocol of Example 2.

The ingredients used are hyaluronic acid (10 g/100 g), stearoyl and palmitoyl chloride used as a 60/40 (w/w) mixture (40 g/100 g) and mica (50 g/100 g).

EXAMPLE 7

Other Products of the Invention from Acacia Gum

The product of the invention is prepared as described in Examples 1 to 5 except that the nature of the hydrophilic polymer is different: acacia gum is used.

The preferred product is prepared by following the protocol of Example 2.

The ingredients used are acacia gum (10 g/100 g), stearoyl and palmitoyl chloride used as a 60/40 (w/w) mixture (40 g/100 g) and a blue iron oxide (50 g/100 g).

EXAMPLE 8

Other Products of the Invention from Polyvinyl Alcohol

The product of the invention is prepared as described in Examples 1 to 5 except that the nature of the hydrophilic polymer is different: commercial polyvinyl alcohol is used.

The preferred product is prepared by following the protocol of Example 2.

The ingredients used are polyvinyl alcohol (10 g/100 g), stearoyl and palmitoyl chloride used as a 60/40 (w/w) mixture (40 g/100 g) and a black iron oxide (50 g/100 g).

EXAMPLE 9

Other Products of the Invention from Polyvinylpyrrolidone

The product of the invention is prepared as described in Examples 1 to 5 except that the nature of the hydrophilic polymer is different: commercial polyvinylpyrrolidone is used.

The preferred product is prepared by following the protocol of Example 2.

The ingredients used are polyvinylpyrrolidone (10 g/100 g), stearoyl and palmitoyl chloride used as a 60/40 (w/w) mixture (40 g/100 g) and a red iron oxide (50 g/100 g).

EXAMPLE 10
Other Products of the Invention from Agar

The product of the invention is prepared as described in Examples 1 to 5 except that the nature of the hydrophilic polymer is different: commercial agar is used.

The preferred product is prepared by following the protocol of Example 2.

The ingredients used are agar (10 g/100 g), stearoyl and palmitoyl chloride used as a 60/40 (w/w) mixture (40 g/100 g) and the organic pigment DC Red 7 (50 g/100 g).

EXAMPLE 11
Other Products of the Invention from Aloe Vera

The product of the invention is prepared as described in Examples 1 to 5 except that the nature of the hydrophilic polymer is different: commercial aloe vera is used.

The preferred product is prepared by following the protocol of Example 2.

The ingredients used are aloe vera (10 g/100 g), stearoyl and palmitoyl chloride used as a 60/40 (w/w) mixture (40 g/100 g) and the organic pigment DC Blue 1 (50 g/100 g).

EXAMPLE 12
Other Products of the Invention from Starch or Maltodextrins

The product of the invention is prepared as described in Examples 1 to 5 except that the nature of the hydrophilic polymer is different: commercial starch, or commercial maltodextrins derived from partial hydrolysis of this starch, are used.

The preferred product is prepared by following the protocol of Example 2.

The ingredients used are starch or its hydrolysis products (10 g/100 g), stearoyl and palmitoyl chloride used as a 60/40 (w/w) mixture (40 g/100 g) and the organic pigment Solvent Red 1 (50 g/100 g).

EXAMPLE 13
Other Products of the Invention from Other Polymers

The product of the invention is prepared as described in Examples 1 to 5 except that the nature of the hydrophilic polymer is different: elastin or hydrolyzates thereof, collagen and gelatin or hydrolyzates thereof, silk and hydrolyzates thereof, alginic acid, guar and quaternized derivatives thereof, chondroitin sulfate, cellulose and derivatives thereof (ethyl cellulose, hydroxyethyl cellulose and hydroxypropyl cellulose in particular), chitosan, hydrolyzates thereof and derivatives thereof such as hydroxypropyl chitosan, carboxyvinylic polymer and proteins of wheat, maize, soya, lupin, pea, bean, horse bean etc., are used. This list does not imply a limitation.

The preferred product is prepared by following the protocol of Example 2.

EXAMPLE 14
"No Transfer" Lipstick

This study was carried out in order to show the advantage of the product of the invention compared with the ingredients of which this invention is composed, taken separately.

To do this, lipsticks which do not transfer when applied e.g. to a white cup (called "no transfer LS" in the text), which are acknowledged to be particularly uncomfortable (dry to the touch, dry and difficult to spread, unpleasant feel, etc.), were prepared with and without the products of the invention, and the above criteria were studied.

Each study was carried out by a standardized adapted procedure and was used to analyze the characteristics of each LS compared with the control.

The products were prepared as described in Example 2 using the following constituents and proportions:

Preparation A: acacia gum (10 g/100 g), stearic and palmitic chains (40 g/100 g), titanium dioxide (50 g/100 g).

Preparation B: acacia gum (30 g/100 g), stearic and palmitic chains (20 g/100 g), titanium dioxide (50 g/100 g).

The products of the invention were used in an amount of 3% in an LS formulation. The complex is introduced at the expense of the percentage of free $TiO_2$ and castor oil, according to the Table I below:

TABLE I

| Ref. | | % of free $TiO_2$ | % of products of the invention | % of acacia gum | % of stearic chains | % of castor oil | Lipstick formulation |
|---|---|---|---|---|---|---|---|
| 1 | CONTROL | 1.5 | / | / | / | 32.91 | qsp 100 |
| 2 | CONTROL for A | 1.5 | / | 0.3 | 1.2 | 29.91 | qsp 100 |
| 3 | CONTROL for B | 1.5 | / | 0.9 | 0.6 | 29.91 | qsp 100 |
| 4 | Product A of the invention | / | 3 | / | / | 29.91 | qsp 100 |
| 5 | Product B of the invention | / | 3 | / | / | 29.91 | qsp 100 |

To be able to compare the tests containing the complex with the control, a strictly identical procedure was followed for each of the tests.

The procedure was defined to allow the complex to swell thoroughly, to disperse and to be correctly integrated into the crystal lattice. To do this, the various ingredients to be used, shown in the Table above, were ground in a triple roll mill (2 passes) in the castor oil. The ground material was left to stand for 24 h.

After the ground material had been heated to 80° C., the other raw materials constituting the lipstick formulation were added individually, after which the pigment compound, previously ground on the triple roll mill (2 passes), was added over 10 min, with agitation.

The product is cast into a mold at 37° C.; the cake is removed after 15 min. After a further 15 min, the mold is placed at −18° C. for 40 min.

Demolding takes place in the cold in order to take advantage of the contraction of the stick.

The various tests performed were observed in comparison with the controls containing no complex, according to the following criteria, Table II:

| | |
|---|---|
| +/− | Identical to the control |
| − | Inferior to the control |
| + | Good |
| ++ | Very good |
| +++ | Excellent |

TABLE II

| | Parameters studied | 1 | 4 | 5 | 2 | 3 |
|---|---|---|---|---|---|---|
| Processing | Appearance of ground material containing complex | / | NTR* | NTR | NTR | NTR |
| | Casting | NTR | +/− | +/− | +/− | +/− |

TABLE II-continued

| | Parameters studied | 1 | 4 | 5 | 2 | 3 |
|---|---|---|---|---|---|---|
| Appearance of stick | Appearance of cake | very friable, dry | correct, less friable | correct, less friable | very friable, dry | very friable, dry |
| | Demolding | NTR | +/− | +/− | +/− | +/− |
| | Dispersion of pigments | NTR | +/− | +/− | − | − |
| | Color rendition | control | +/− | − | − | − |
| Application | Spread Slide | drags, difficult to spread, dry | ++ | +++ spread, | drags, difficult to spread, dry | drags, difficult to spread, dry |
| | Ability to deposit | average to poor | ++ | ++ | average to poor | average to poor |
| | Use comfort | insufficient, does not deposit film | ++ | +++ | insufficient, does not deposit film | insufficient, does not deposit film |
| Properties after application | Color rendition | control | + | ++ | − | − |
| | Gloss | average | + | + | − | − |
| | Stability | good | + | + | +/− | +/− |

*NTR = nothing to report

EXAMPLE 15
"No Transfer" Lipstick

This study was carried out in order to show the advantage of the product of the invention compared with the ingredients of which this invention is composed, taken separately.

To do this, lipsticks which do not transfer when applied e.g. to a white cup (called "no transfer LS" in the text), which are acknowledged to be particularly uncomfortable (dry to the touch, dry and difficult to spread, unpleasant feel, etc.), were prepared with and without the products of the invention, and the above criteria were studied.

Each study was carried out by a standardized adapted procedure and was used to analyze the characteristics of each LS compared with the control.

The products were prepared as described in Example 1 using the following constituents and proportions:

Preparation A: gum lac (10 g/100 g), stearic and palmitic chains (40 g/100 g), titanium dioxide (50 g/100 g).

Preparation B: gum lac (30 g/100 g), stearic and palmitic chains (20 g/100 g), titanium dioxide (50 g/100 g).

The products of the invention were used in an amount of 3% in an LS formulation. The complex is introduced at the expense of the percentage of free $TiO_2$ and castor oil, according to the Table III below:

TABLE III

| Ref. | | % of free $TiO_2$ | % of products of the invention | % of gum lac | % of stearic chains | % of castor oil | Lipstick formulation |
|---|---|---|---|---|---|---|---|
| 1 | CONTROL | 1.5 | / | / | / | 31.41 | qsp 100 |
| 2 | CONTROL for A | 1.5 | / | 0.3 | 1.2 | 29.91 | qsp 100 |
| 3 | CONTROL for B | 1.5 | / | 0.9 | 0.6 | 29.91 | qsp 100 |
| 4 | Product A of the invention | / | 3 | / | / | 29.91 | qsp 100 |
| 5 | Product B of the invention | / | 3 | / | / | 29.91 | qsp 100 |

A procedure identical to that described in Example 14 was followed for each of the tests.

The various tests performed were observed in comparison with the controls containing no complex, according to the following criteria, Table IV:

| | |
|---|---|
| +/− | Identical to the control |
| − | Inferior to the control |
| + | Good |
| ++ | Very good |
| +++ | Excellent |

TABLE IV

| | Parameters studied | 1 | 4 | 5 | 2 | 3 |
|---|---|---|---|---|---|---|
| Processing | Appearance of ground material containing products | / | NTR | NTR | NTR | NTR |
| | Casting | NTR | +/− | +/− | +/− | +/− |
| | Appearance of cake | very friable, dry | less friable | less friable | very friable, dry | very friable, dry |
| | Demolding | NTR | +/− | +/− | +/− | +/− |
| Appearance of stick | Dispersion of pigments | NTR | + | + | − | − |
| | Color rendition | control | + | + | − | − |
| Application | Spread Slide | drags, difficult | ++ | + | drags, difficult | drags, difficult |

TABLE IV-continued

| Parameters studied | | 1 | 4 | 5 | 2 | 3 |
|---|---|---|---|---|---|---|
| | | to spread, dry average to poor | | | to spread, dry average to poor | to dry average to poor |
| | Ability to deposit | | ++ | + | | |
| | Use comfort | Insufficient, does not deposit film | ++ | + | Insufficient, does not deposit film | Insufficient, does not deposit film |
| Properties after application | Color rendition | control | + | +/− | − | − |
| | Gloss | average | + | + | − | − |
| | Stability | good | + | +/− | +/− | +/− |

EXAMPLE 16

"No Transfer" Lipstick

This study was carried out in order to show the comparative advantage of the products of the invention when the nature of the hydrophilic polymer is modified.

To do this, lipsticks which do not transfer when applied e.g. to a white cup (called "no transfer LS" in the text), which are acknowledged to be particularly uncomfortable (dry to the touch, dry and difficult to spread, unpleasant feel, etc.), were prepared with and without the products of the invention, and the above criteria were studied.

Each study was carried out by a standardized adapted procedure and was used to analyze the characteristics of each LS compared with the control.

The products were prepared as described in Example 2 using the following constituents and proportions:

Preparation A: gum lac (7.5 g/100 g) and polyvinyl alcohol (22.5 g/100 g), stearic and palmitic chains (20 g/100 g), commercial nylon beads (Orgasol, CECA France) (50 g/100 g).

Preparation B: polyvinyl alcohol (30 g/100 g), stearic and palmitic chains (20 g/ 100 g), commercial nylon beads (Orgasol, CECA France) (50 g/100 g).

The products of the invention were used in an amount of 3% in an LS formulation. The complex is introduced at the expense of the percentage of nylon beads and silicone oil, according to the Table V below:

TABLE V

| Ref. | | % of nylon beads | % of products of the invention | % of silicone oil | Lipstick formulation |
|---|---|---|---|---|---|
| 1 | CONTROL | 1.5 | / | 31.41 | qsp 100 |
| 2 | Product A of the invention | / | 3 | 29.91 | qsp 100 |
| 3 | Product B of the invention | / | 3 | 29.91 | qsp 100 |

A procedure identical to that described in Example 14 was followed for each of the tests.

The various tests performed were observed in comparison with the controls containing no complex, according to the following criteria table VI:

| +/− | Identical to the control |
|---|---|
| − | Inferior to the control |
| + | Good |
| ++ | Very good |
| +++ | Excellent |

TABLE VI

| | Parameter | 1 | 2 | 3 |
|---|---|---|---|---|
| Processing | Appearance of ground material containing complex | / | NTR | NTR |
| | Casting Appearance of cake | NTR very friable, dry | +/− correct, less friable | +/− correct, less friable |
| | Demolding | NTR | +/− | +/− |
| Appearance of stick | Dispersion of pigments | NTR | +/− | +/− |
| | Color rendition | control | +/− | +/− |
| Application | Spread | drags, difficult to spread, dry | +++ | + |
| | Slide Ability to deposit | average to poor | +++ | ++ |
| | Use comfort | insufficient, does not deposit film | ++ | ++ |
| Properties after application | Color rendition | control | ++ | + |
| | Gloss | average | +++ | +++ |
| | Taste | vanilla | +/− | +/− |
| | Stability | good | + | +/− |
| Physical properties | Hardness | pressure resistance | +/− | +/− |
| | Plasticity | good | + | +/− |
| | Friability | none | +/− | +/− |

In conclusion, these various Examples provide confirmation that the improvement in the gloss and application of the LS, in terms of the slide and spread, is indeed brought about by the combination of hydrophilic molecule, fatty acid and pigment or filler (as appropriate).

EXAMPLE 17

Use of the products of the invention in cosmetic or pharmaceutical formulations of the oil-in-water emulsion type Formulation 17a:

| A | Water | qsp100 |
|---|---|---|
| | Butylene glycol | 2 |
| | Glycerol | 3 |
| | Sodium dihydroxycetyl phosphate, isopropyl hydroxycetyl Ether | 2 |
| B | Glycol stearate SE | 14 |
| | Triisononanoin | 5 |
| | Octyl cocoate | 6 |
| C | Butylene glycol, methylparaben, ethylparaben, propylparaben pH adjusted to 5.5 | 2 |
| D | Products of the invention | 0.01–10% |

| Formulation 17b: | | |
|---|---|---|
| A | Water | qsp 100 |
| | Butylene glycol | 2 |
| | Glycerol | 3 |
| | Polyacrylamide, isoparaffin, laureth-7 | 2.8 |
| B | Butylene glycol, methylparaben, ethylparaben, propylparaben | 2 |
| | Phenoxyethanol, methylparaben, propylparaben, butylparaben, ethylparaben | 0.5 |
| C | Butylene glycol | 0.5 |
| D | Products of the invention | 0.01–10% |

| Formulation 17c: | | |
|---|---|---|
| A | Carbomer | 0.50 |
| | Propylene glycol | 3 |
| | Glycerol | 5 |
| | Water | qsp 100 |
| B | Octyl cocoate | 5 |
| | Bisabolol | 0.30 |
| | Dimethicone | 0.30 |
| C | Sodium hydroxide | 1.60 |
| D | Phenoxyethanol, methylparaben, propylparaben, butylparaben, ethylparaben | 0.50 |
| E | Perfume | 0.30 |
| F | Products of the invention | 0.01–10% |

EXAMPLE 18 OF THE INVENTION

| Use of the products of the invention in a formulation of the water-in-oil type | | |
|---|---|---|
| A | PEG 30 dipolyhydroxystearate | 3 |
| | Capric triglycerides | 3 |
| | Cetearyl octanoate | 4 |
| | Dibutyl adipate | 3 |
| | Grape seed oil | 1.5 |
| | Jojoba oil | 1.5 |
| | Phenoxyethanol, methylparaben, propylparaben, butylparaben, ethylparaben | 0.5 |
| B | Glycerol | 3 |
| | Butylene glycol | 3 |
| | Magnesium sulfate | 0.5 |
| | EDTA | 0.05 |
| | Water | qsp 100 |
| C | Cyclomethicone | 1 |
| | Dimethicone | 1 |
| D | Perfume | 0,3 |
| E | Products of the invention | 0.01–10% |

EXAMPLE 19 OF THE INVENTION

| Use of the products of the invention in a formulation of the shampoo or shower gel type | | |
|---|---|---|
| A | Xanthan gum | 0.8 |
| | Water | qsp 100 |
| B | Butylene glycol, methylparaben, ethylparaben, propylparaben | 0.5 |
| | Phenoxyethanol, methylparaben, propylparaben, butylparaben, and ethylparaben | 0.5 |
| C | Citric acid | 0.8 |
| D | Sodium laureth sulfate | 40.0 |
| E | Product of the invention | 0.01–10% |

EXAMPLE 20 OF THE INVENTION

| Use of the products of the invention in a formulation of the anhydrous product type (lipsticks, make-up foundations, fluid powders, pressed powders) | | |
|---|---|---|
| A | Mineral wax | 17.0 |
| | Isostearyl isostearate | 31.5 |
| | Propylene glycol dipelargonate | 2.6 |
| | Propylene glycol isostearate | 1.7 |
| | PEG 8 beeswax | 3.0 |
| | Hydrogenated palm kernel oil, glycerides, hydrogenated palm glycerides | 3.4 |
| | Lanolin oil | 3.4 |
| | Sesame oil | 1.7 |
| | Cetyl lactate | 1.7 |
| | Mineral oil, lanolin alcohol | 3.0 |
| B | Castor oil | qsp 100 |
| | Titanium dioxide | 3.9 |
| | CI 15850:1 | 0.616 |
| | CI 45410:1 | 0.256 |
| | CI 19140:1 | 0.048 |
| | CI 77491 | 2.048 |
| C | Products of the invention | 0.01–5% |

EXAMPLE 21 OF THE INVENTION

| Use of the products of the invention in an aqueous gel formulation (eye contour gels, slimming gels, etc.) | | |
|---|---|---|
| A | Water | qsp 100 |
| | Carbomer | 0.5 |
| | Butylene glycol | 15 |
| | Phenoxyethanol, methylparaben, propylparaben, butylparaben, and ethylparaben | 0.5 |
| B | Products of the invention | 0.01–10% |

EXAMPLE 22

Evaluation of the Cosmetic Acceptance of a Preparation Containing the Subject of the Invention The toxicology tests were performed on the compound obtained according to Example 2, incorporated at 10% in a 0.5% xanthan gel, by means of an ocular evaluation in the rabbit, by a study of the absence of abnormal toxicity of a single oral dose in the rat, and by a study of the sensitizing power in the guinea-pig.

Evaluation of the Primary Skin Irritation in the Rabbit

The preparations described above are applied undiluted at a dose of 0.5 ml to the skin of 3 rabbits using the method recommended by the OECD directive relating to the study of "the acute irritant/corrosive effect on the skin".

The products are classified according to the criteria defined by the decree of Jan. 2, 1982 published in the JORF (Official Gazette of the French Republic) of 21/02/82.

The results of these tests afforded the conclusion that the preparations were classified as non-irritant on the skin.

Evaluation of the Ocular Irritation in the Rabbit

The preparations described above were instilled pure, all at once, at a dose of 0.1 ml into the eyes of 3 rabbits using the method recommended by OECD directive no. 405 of Feb. 24, 1987 relating to the study of "the acute irritant/corrosive effect on the eyes".

The results of this test afford the conclusion that the preparations can be considered as non-irritant on the eyes, used pure or undiluted, in terms of directive 91/326 EEC.

Test on the Absence of Abnormal Toxicity of a Single Oral Dose in the Rat

The preparations described were administered orally, all at once, at a dose of 5 g/kg body weight to 5 male rats and 5 female rats according to a protocol based on OECD directive no. 401 of Feb. 24, 1987 and adapted to cosmetic products.

The $LD_0$ and $LD_{50}$ are found to be greater than 5000 mg/kg, so the preparations tested are not classified as being dangerous by ingestion.

Evaluation of the Skin Sensitizing Potential in the Guinea-pig

The preparations described are subjected to the maximization test described by Magnusson and Kligmann, the protocol of which is consistent with OECD directive no. 406.

The preparations are classified as non-sensitizing by contact with the skin.

EXAMPLE 23

Products of the invention manufactured according to Example 1 with the following proportions:
Product A: hyaluronic acid 10 g/100 g, stearic and palmitic chains 40 g/100 g, mica 50 g/100 g
Product B: hyaluronic acid 15 g/100 g, stearic and palmitic chains 35 g/100 g, mica 50 g/100 g
Product C: hyaluronic acid 1 g/100 g, acacia gum 14 g/100 g, stearic and palmitic chains 35 g/100 g, mica 50 g/100 g Products of the invention manufactured according to Example 2 with the following proportions:
Product D: hyaluronic acid 10 g/100 g, stearic and palmitic chains 40 g/100 g, mica 50 g/100 g
Product E: hyaluronic acid 15 g/100 g, stearic and palmitic chains 35 g/100 g, mica 50 g/100 g
Product F: hyaluronic acid 1 g/100 g, acacia gum 14 g/100 g, stearic and palmitic chains 35 g/100 g, mica 50 g/100 g After thorough drying, the water uptake capacity of these products was measured. To do this, the products were first brought back to room temperature and weighed, and then brought into contact with the atmosphere for 24 h and weighed again. The results are reported in the Table below in g of water adsorbed per 100 g of product of the invention. The greater the capacity of the treated pigments to trap water, the greater will be the moisturizing power of the pigments in a formulation:
Product A: 3.1
Product B: 5.2
Product C: 1.5
Product D: 3.2
Product E: 5.1
Product F: 1.4
Untreated mica: 0.08

EXAMPLE 24

Products of the invention manufactured according to Example 1 with the following proportions:

Product A: chondroitin sulfate 20 g/100 g, stearic and palmitic chains 30 g/100 g, $TiO_2$ 50 g/100 g
Product B: gum lac 20 g/100 g, stearic and palmitic chains 30 g/100 g, ZnO 50 g/100 g
Product C: guar gum 20 g/100 g, stearic and palmitic chains 30 g/100 g, DC Red 7 50 g/100 g
Product D: sodium alginate 20 g/100 g, stearic and palmitic chains 30 g/100 g, black iron oxide 50 g/100 g
Product E: chitosan 20 g/100 g, stearic and palmitic chains 30 g/100 g, yellow iron oxide 50 g/100 g
Product F: wheat protein 20 g/100 g, stearic and palmitic chains 30 g/100 g, green chromium oxide 50 g/100 g
Product G: hydroxypropyl cellulose 20 g/100 g, stearic and palmitic chains 30 g/100 g, powdered oyster shells 50 g/100 g
Product H: carob gum 20 g/100 g, stearic and palmitic chains 30 g/100 g, powdered nylon/polyamide 50 g/100 g
Product I: fish gelatin 20 g/100 g, stearic and palmitic chains 30 g/100 g, powdered polyester 50 g/100 g
Product J: fish collagen 20 g/100 g, stearic and palmitic chains 30 g/100 g, interferential pigment 50 g/100 g
Product K: lupin protein 20 g/100 g, stearic and palmitic chains 30 g/100 g, powdered silk fibers 50 g/100 g
Product L: soya protein 20 g/100 g, stearic and palmitic chains 30 g/100 g, sun filter in the form of nanoparticles (Tinosorb®, Ciba) 50 g/100 g
Product M: pea protein 20 g/100 g, stearic and palmitic chains 30 g/100 g, talcum 50 g/100 g
Product N: sunflower protein 20 g/100 g, stearic and palmitic chains 30 g/100 g, silica 50 g/100 g
Product O: maize protein 20 g/100 g, stearic and palmitic chains 30 g/100 g, cellulose beads 50 g/100 g
Product P: bean protein 20 g/100 g, stearic and palmitic chains 30 g/100 g, silica beads 50 g/100 g
Product Q: horse bean protein 20 g/100 g, stearic and palmitic chains 30 g/100 g, water-insoluble active principle such as ursolic acid 50 g/100 g Products of the invention manufactured according to Example 2 with the following proportions:
Product R: chondroitin sulfate 20 g/100 g, stearic and palmitic chains 30 g/100 g, $TiO_2$ 50 g/100 g
Product S: gum lac 20 g/100 g, stearic and palmitic chains 30 g/100 g, ZnO 50 g/100 g
Product T: guar gum 20 g/100 g, stearic and palmitic chains 30 g/100 g, DC Red 7 50g/100 g
Product U: sodium alginate 20 g/100 g, stearic and palmitic chains 30 g/100 g, black iron oxide 50 g/100 g
Product V: chitosan 20 g/100 g, stearic and palmitic chains 30 g/100 g, yellow iron oxide 50 g/100 g
Product W: wheat protein 20 g/100 g, stearic and palmitic chains 30 g/100 g, green chromium oxide 50 g/100 g
Product X: hydroxypropyl cellulose 20 g/100 g, stearic and palmitic chains 30 g/100 g, powdered oyster shells 50 g/100 g
Product Y: carob gum 20 g/100 g, stearic and palmitic chains 30 g/100 g, powdered nylon/polyamide 50 g/ 100 g
Product Z: fish gelatin 20 g/100 g, stearic and palmitic chains 30 g/100 g, powdered polyester 50 g/100 g
Product AA: fish collagen 20 g/100 g, stearic and palmitic chains 30 g/100 g, interferential pigment 50 g/100 g
Product AB: lupin protein 20 g/100 g, stearic and palmitic chains 30 g/100 g, powdered silk fibers 50 g/100 g
Product AC: soya protein 20 g/100 g, stearic and palmitic chains 30 g/100 g, sun filter in the form of nanoparticles (Tinosorb®, Ciba) 50 g/100 g
Product AD: pea protein 20 g/100 g, stearic and palmitic chains 30 g/100 g, talcum 50 g/100 g Product AE: sunflower protein 20 g/100 g, stearic and palmitic chains 30 g/100 g, silica 50 g/100 g Product AF: maize protein 20 g/100 g, stearic and palmitic chains 30 g/100 g, cellulose beads .50 g/100 g Product AG: bean protein 20 g/100 g, stearic and palmitic chains 30 g/100 g, silica beads 50 g/100 g Product AH: horse bean protein 20 g/100 g, stearic and palmitic chains 30 g/100 g, water-insoluble active principle such as ursolic acid 50 g/100 g After thorough drying, the water uptake capacity of these products was measured. To do this, the products were first brought back to room temperature and weighed, and then brought into contact with the atmosphere for 24 h and weighed again. The results are reported in the Table below in g of water adsorbed per 100 g of product of the invention. The greater the capacity of the treated pigments to trap water, the greater will be the moisturizing power of the pigments in a formulation:

| Example ref. | g of water per 100 g |
| --- | --- |
| A to Q: | 1–20 |
| R to AH: | 1–20 |
| Uncoated pigment or article: | 0.01–0.4 |

EXAMPLE 25

Products of the invention manufactured according to Example 1 with the following proportions:

zinc oxide (50 g/100 g), gum lac (20 g/100 g), stearic and palmitic chains (30 g/100 g)

Two make-up foundation formulations were prepared, incorporating in one case each of the individual compounds described above and in the other case the product of the invention described in the present Example.

The sensory characteristics of these two formulations were evaluated by a panel of 15 expert volunteers and scored on a scale of 1 to 15, 1 representing the worst score. The means of these evaluations are shown on Table VII below:

TABLE VII

| | Just after application | | 5 hours after application | |
| --- | --- | --- | --- | --- |
| | Control | Product of the invention according to this Example | Control | Product of the invention according to this Example |
| Spreadability | 9.7 | 10.9 | / | / |
| Coverage | 11.3 | 12.5 | 10.9 | 11.4 |
| Uniformity | 11 | 11.9 | 10.3 | 11.7 |
| Vividness of color | 7.2 | 9.2 | / | / |
| Migration of product | / | / | 5 | 4.6 |

(/: not evaluated)

Compared with the various ingredients taken separately, the product of the invention improves the spreadability of make-up foundations containing it, improves the coverage and the uniformity of the color (initially as well as 5 h after application), improves the vividness of the color and reduces its migration on the skin 5 hours after application.

Consequently, as well as providing moisturizing properties, the products of the invention improve (or preserve, which is already unexpected for those skilled in the art) the organoleptic properties of formulations containing them.

EXAMPLE 25A

Products of the invention manufactured according to Example 1 with the following proportions:

titanium dioxide (50 g/100 g), acacia gum (20 g/100 g), stearic and palmitic chains (30 g/100 g)

Two lipstick formulations were prepared, incorporating in one case each of the individual compounds described above and in the other case the product of the invention described in the present Example.

The sensory characteristics of these two formulations were evaluated by a panel of 15 expert volunteers and scored on a scale of 1 to 15, 1 representing the worst score. The means of these evaluations are shown on Table VIII below:

TABLE VIII

| | Just after application | | 5 hours after application | |
| --- | --- | --- | --- | --- |
| | Control | Product of the invention according to this Example | Control | Product of the invention according to this Example |
| Slide | 3.3 | 4.6 | / | / |
| Amount deposited | 8.4 | 9.5 | / | / |
| Coverage | 13.1 | 13.3 | 9.9 | 10.1 |
| Vividness of color | 10.4 | 11.2 | / | / |
| Sharpness of contour | 10.6 | 10.7 | / | / |

(/: not evaluated)

Compared with the various ingredients taken separately, the product of the invention improves the slide of lipsticks containing it, improves the amount deposited, improves the coverage and the vividness of the color (initially as well as 5 h after application) and improves the sharpness of the contours after application of the lipsticks.

Consequently, as well as providing moisturizing properties, the products of the invention improve (or preserve, which is already unexpected for those skilled in the art) the organoleptic properties of formulations containing them.

What is claimed is:

1. A water-insoluble, coated, solid particle, comprising: a water-insoluble solid particle which is coated with at least one layer of at least one product resulting from the reaction between:
   a. at least one molecule hydratable in contact with water selected from the group consisting of a peptide, a protein, a polysaccharide, an oligosaccharide, a gum, a vinylic polymer and a fluorinated polymer; and
   b. at least one lipophilic molecule
   wherein the at least one lipophilic molecule is grafted onto the hydratable molecule.

2. The coated solid particle according to claim 1, wherein the lipophilic molecule is a reactive form of a hydrocarbon organic molecule having from 4 to 30 carbon atoms which is reacted in a reactive form with the molecule hydratable in contact with water.

3. The coated solid particle according to claim 1, wherein the water-insoluble solid particle is selected from the group consisting of an organic pigment, a mineral pigment, a mineral filler, a physical sun filter, a metal oxide and a chemical sun filter.

4. The coated solid particle of claim 3, wherein the mineral filler is talcum.

5. The coated solid particle of claim 3, wherein the metal oxide is selected from the group consisting of zinc oxide, titanium dioxide and boron nitride.

6. The coated solid particle of claim 1, wherein the molecule hydratable in contact with water is a peptide with a molecular weight of less than 5000 Daltons.

7. The coated solid particle according to claim 6, wherein said protein has an average molecular weight equal to or greater than 5000 Daltons and less than 1,000,000 Daltons.

8. The coated solid particle of claim 7, wherein said protein has an average molecular weight less than 300,000 Daltons.

9. The coated solid particle of claim 6, wherein said protein is selected from the group consisting of collagen, gelatin, albumin, ovalbumin, elastin, reticulin, fibronectin, keratin, silk, laminin, desmosin, isodesmosin, a proteoglycan of the extracellular matrix, a glycosaminoglycan, hyaluronic acid, casein, lactalbumin, lactoglobulin, an enzyme extracted from animal tissues, a protein extracted from a plant, a protein extracted from wheat protein, a unicellular or a multicellular alga protein, a maize protein, a pea protein, a lupin protein, a bean protein, a horse bean protein, a cotton protein, an almond protein, a soya protein, a sunflower protein, an alfalfa protein, an oat protein, cellulose and alkyl substituted cellulose, hydroxyalkyl cellulose, ethylcellulose, hydroxyethyl cellulose, propyl cellulose, hydroxypropyl cellulose, chitosan, alkyl substituted chitosan and hydroxyalkyl chitosan, propyl chitosan, hydroxypropyl chitosan, starch, maltodextrin, a polyvinyl alcohol, a polyvinylpyrrolidone, and mixtures thereof.

10. The coated solid particle of claim 1, wherein said lipophilic molecule is a hydrophobic, $C_4$–$C_{30}$ lipophilic fatty molecule.

11. The coated solid particle of claim 1, wherein said lipophilic molecule is a saturated or unsaturated $C_4$–$C_{30}$ lipophilic fatty molecule.

12. The coated solid particle of claim 1, wherein said lipophilic molecule is linear, branched or cyclic $C_4$–$C_{30}$ lipophilic fatty molecule.

13. The coated solid particle of claim 11, wherein said lipophilic fatty molecule is a reactive form selected from the group consisting of a $C_4$–$C_{30}$ fatty alkyl halide, a $C_4$–$C_{30}$ fatty acid halide and a $C_4$–$C_{30}$ fatty acid anhydride.

14. The coated solid particle of claim 1, wherein said lipophilic molecule is selected from the group consisting of a $C_4$–$C_{30}$ fatty acid, a $C_4$–$C_{30}$ fatty acid salt, a $C_4$–$C_{30}$ fatty acid ester; a $C_4$–$C_{30}$ fatty alcohol, a $C_4$–$C_{30}$ fatty alcohol ester, a $C_4$–$C_{30}$ fatty amine, a $C_4$–$C_{30}$ fatty amide, and mixtures thereof.

15. The coated solid particle of claim 1, wherein said lipophilic molecule is selected from the group consisting of butyric acid, a butyric acid ester, pentanoic acid, a pentanoic acid ester, hexanoic acid, a hexanoic acid ester, heptanoic acid, a heptanoic acid ester, octanoic acid, an octanoic acid ester, nonanoic acid, a nonanoic acid ester, decanoic acid, a decanoic acid ester, dodecanoic acid, a dodecanoic acid ester, lauric acid, a lauric acid ester, myristic acid, a myristic acid ester, palmitic acid, a palmitic acid ester, stearic acid, a stearic acid ester, ricinoleic acid, a ricinoleic acid ester, oleic acid, an oleic acid ester, linoleic acid, a linoleic acid ester, a linolenic acid, linolenic acid ester, undecylenic acid, an undecylenic acid ester, laurylamine, hexadecylamine, decyl alcohol, and mixtures thereof.

16. The coated solid particle of claim 1, wherein the molecule hydratable in contact with water is first introduced into an aqueous medium, in which it is dissolved or dispersed, after which it is reacted with said lipophilic molecule in reactive form until said reaction product is formed, and then said water-insoluble solid particles are added to the medium containing the reaction product and are dispersed in said medium, thereby having said water-insoluble solid particle coated with said reaction product.

17. The coated solid particle of claim 1, wherein the molecule hydratable in contact with water is introduced into an aqueous medium until it is dissolved or dispersed, then said water-insoluble solid particles are dispersed in said aqueous medium, and then said lipophilic molecule in reactive form is introduced into the aqueous medium to give said reaction product, thereby having said water-insoluble solid particle coated with said reaction product.

18. The coated solid particle of claim 17, wherein said aqueous medium containing said water-insoluble solid particles coated with said reaction product is adjusted to a pH compatible with an industrial use selected from the group consisting of a cosmetic use, a pharmaceutical use, a food use and an agricultural use.

19. The coated solid particle of claim 18, wherein said aqueous medium containing said water-insoluble solid particles coated with said reaction product is adjusted to a pH compatible with an industrial use selected from the group consisting of a cosmetic use, a pharmaceutical use, a food use and an agricultural use.

20. The coated solid particle of claim 17, wherein said aqueous medium containing said water-insoluble solid particle coated with said reaction product is dried.

21. The coated solid particle of claim 20, wherein said drying is selected from the group consisting of: atomization, lyophilization and dehydration under vacuum.

22. The coated solid particle of claim 18, wherein said aqueous medium containing said water-insoluble solid particles coated with said reaction product is dried.

23. The coated solid particle of claim 20, wherein said drying is selected from the group consisting of: atomization, lyophilization and dehydration under vacuum.

24. The coated solid particle of claim 21, wherein said dried product is ground until the average particle size is not greater than about 200 µm.

25. The coated solid particle of claim 23, wherein said dried product is ground until the average particle size is not greater than about 200 µm.

26. A coated water-insoluble pigment comprising: at least one water insoluble pigment which is coated with at least one layer of at least one product resulting from the reaction between:
   a) at least one molecule hydratable in contact with water selected from the group consisting of a peptide, a protein, a polysaccharide, an oligosaccharide, a gum, a vinylic polymer and a fluorinated polymer; and
   b) at least one lipophilic molecule.

27. A coated water-insoluble solid particle comprising: at least one water-insoluble solid particle coated with at least one layer of at least one product resulting from the reaction between
   a) at least one hydratable molecule selected from the group consisting of a peptide, a protein, a polysaecharide, an oligosaccharide, a gum, a vinylic polymer and a fluorinated polymer; and
   b) at least one lipophilic molecule, wherein said lipophilic molecule comprises a halide of a fatty acid selected from the group consisting of butyric acid, capric acid, caprylic acid, decanoic acid, lauric acid, stearic acid, myristic acid, palmitic acid, oleic acid, linoleic acid, linolenic acid, undecylenic acid and undecanoic acid;

wherein the at least one lipophilic molecule is grafted onto the hydratable molecule;

wherein said solid particle is selected from the group consisting of a white organic pigment, a colored organic pigment, a white mineral pigment, a colored mineral pigment, titanium dioxide, zinc oxide, chromium oxide a black iron oxide, a yellow iron oxide, a blue iron oxide, a mineral filler, a make-up mineral filler, talcum, kaolin, mica, boron nitride, nylon beads, silica and silica beads.

28. The coated water-insoluble solid particle of claim 27, wherein said hydratable molecule comprises at least one gum lac.

29. The coated water-insoluble solid particle of claim 28, wherein said hydratable molecule comprises hyaluronic acid.

30. The coated water-insoluble solid particle of claim 27, wherein said hydratable molecule comprises acacia gum.

31. The coated water-insoluble solid particle of claim 27, wherein said hydratable molecule comprises polyvinyl alcohol.

32. The coated water-insoluble solid particle of claim 27, wherein said hydratable molecule comprises polyvinylpyrolidone.

33. The coated water-insoluble solid particle of claim 27, wherein said hydratable molecule comprises an agar.

34. The coated water-insoluble solid particle of claim 27, wherein said hydratable molecule comprises an aloe.

35. The coated water-insoluble solid particle of claim 27, wherein said hydratable molecule comprises starch or maltodextrin.

36. A cosmetic composition comprising:

at least one coated water-insoluble solid particle, comprising at least one water-insoluble solid particle coated with at least one layer of at least one reaction product resulting from the reaction between a molecule hydratable in contact with water selected from the group consisting of a peptide, a protein, a polysaccharide, an oligosaccharide, a gum, a vinylic polymer and a fluorinated polymer; and at least one lipophilic molecule, wherein the at least one lipophilic molecule is grafted onto the hydratable molecule; and at least one cosmetically acceptable excipient.

37. A pharmaceutical composition comprising:

at least one coated water-insoluble solid particle, comprising at least one water-insoluble solid particle coated with at least one layer of at least one reaction product resulting from the reaction between a molecule hydratable in contact with water selected from the group consisting of a peptide, a protein, a polysaccharide, an oligosaccharide, a gum, a vinylic polymer and a fluorinated polymer; and at least one lipophilic molecule, wherein the at least one lipophilic molecule is grafted onto the hydratable molecule; and at least one pharmaceutically acceptable excipient.

38. A food composition comprising:

at least one water-insoluble solid particle acceptable in food, coated with at least one layer of at least one reaction product resulting from the reaction between a molecule hydratable in contact with water and at least one lipophilic molecule, wherein the at least one lipophilic molecule is grafted onto the hydratable molecule; and at least one food compatible product.

39. An agricultural composition comprising:

at least one coated water-insoluble solid particle, comprising at least one water-insoluble solid particle coated with at least one layer of at least one reaction product resulting from the reaction between at least one molecule hydratable in contact with water and at least one lipophilic molecule, wherein the at least one lipophilic molecule is grafted onto the hydratable molecule; and at least one agriculturally acceptable excipient.

40. A process for the manufacture of coated water-insoluble solid particles comprising:

coating a water-insoluble solid particle with a reaction product, wherein said reaction product results from the reaction between a molecule hydratable in contact with water selected from the group consisting of a peptide, a protein, a polysaccharide, an oligosaccharide, a gum, a vinylic polymer and a fluorinated polymer; and a lipophilic molecule, wherein lipophilic molecule is grafted onto the hydratable molecule in an aqueous medium.

41. The process of claim 40, wherein said reaction product is formed and then mixed with said solid particle.

42. The process of claim 40, wherein said solid particle is mixed before formation of said reaction product.

43. A cosmetic composition comprising at least one coated water-insoluble solid particle of claim 28 at least one cosmetically acceptable excipient.

44. A cosmetic composition comprising at least one coated water-insoluble solid particle of claim 29 and at least one cosmetically acceptable excipient.

45. A cosmetic composition comprising at least one coated water-insoluble solid particle of claim 30 and at least one cosmetically acceptable excipient.

46. A cosmetic composition comprising at least one coated water-insoluble solid particle of claim 31 and at least one cosmetically acceptable excipient.

47. A cosmetic composition comprising at least one coated water-insoluble solid particle of claim 32 and at least one cosmetically acceptable excipient.

48. A cosmetic composition comprising at least one coated water-insoluble solid particle of claim 33 and at least one cosmetically acceptable excipient.

49. A cosmetic composition comprising at least one coated water-insoluble solid particle of claim 34 and at least one cosmetically acceptable excipient.

50. A cosmetic composition comprising at least one coated water-insoluble solid particle of claim 35 and at least one cosmetically acceptable excipient.

* * * * *